(12) United States Patent
Breen et al.

(10) Patent No.: US 6,547,971 B2
(45) Date of Patent: *Apr. 15, 2003

(54) METHODS OF USING HOP ACIDS TO CONTROL ORGANISMS

(75) Inventors: Alexander W. Breen, Jacksonville, FL (US); John M. Cronan, Jr., Jacksonville, FL (US); Phillip S. Davis, Jacksonville, FL (US); Michael J. Mayer, Jacksonville, FL (US); Freddie L. Singleton, Jacksonville, FL (US)

(73) Assignee: Hercules Incorporated, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/521,222

(22) Filed: Mar. 8, 2000

(65) Prior Publication Data

US 2003/0015480 A1 Jan. 23, 2003

(51) Int. Cl.$^7$ .................................................. C02F 1/50
(52) U.S. Cl. ...................... 210/764; 162/161; 422/28; 424/778; 424/725; 514/690
(58) Field of Search ................. 210/698, 764; 162/161; 514/690; 422/28; 424/725, 778

(56) References Cited

U.S. PATENT DOCUMENTS

| | | | |
|---|---|---|---|
| 2,929,758 A | 3/1960 | Buckman et al. | 162/161 |
| 3,486,906 A | 12/1969 | Todd, Jr. et al. | 99/50.5 |
| 3,558,326 A | 1/1971 | Westermann et al. | 99/50.2 |
| 3,798,332 A | 3/1974 | Westerman et al. | 426/29 |
| 3,949,092 A | 4/1976 | Mitchell | 426/16 |
| 3,965,188 A | 6/1976 | Westermann et al. | 426/329 |
| 3,973,052 A | 8/1976 | Mitchell | 426/592 |
| 4,002,683 A | 1/1977 | Todd, Jr. | 260/586 D |
| 4,247,483 A | 1/1981 | Baker et al. | 568/341 |
| 4,298,626 A | 11/1981 | Laws et al. | 426/600 |
| 4,395,431 A | 7/1983 | Lance et al. | 426/600 |
| 4,844,939 A | 7/1989 | Todd, Jr. | 426/600 |
| 4,855,296 A | 8/1989 | Donofrio et al. | 514/241 |
| 4,918,240 A | 4/1990 | Todd, Jr. et al. | 568/366 |
| 5,082,975 A | 1/1992 | Todd, Jr. et al. | 568/315 |
| 5,286,506 A | 2/1994 | Millis et al. | 426/335 |
| 5,370,863 A | 12/1994 | Barney et al. | 424/9 |
| 5,455,038 A | 10/1995 | Barney et al. | 424/405 |
| 6,379,720 B1 * | 4/2002 | Cooper et al. | 424/405 |

FOREIGN PATENT DOCUMENTS

| | | |
|---|---|---|
| JP | 9-67250 | 3/1997 |
| WO | 97 31630 | 9/1997 |
| WO | 97/31630 | 9/1997 |

(List continued on next page.)

OTHER PUBLICATIONS

Abstract, G. J. Haas et al., "Antimircobial Activity of Hop Resins" vol. 57, No. 1, 1994, pp. 59–61.

Abstract, Stephen, T E et al. "Antimicrobial Activity of the Semisynthetic Compound, Hexahydrocolupulone." abstract, Journal of Antimicrobial Chemotherapy, vol. 42, No. 4, Oct. 1998 (1998010), pp. 519–522, ISSN 0305–7553.

Abstract, Mizobuchi, E.etal., "Antifungal Activities of Hop Humulus–Lupulus Bitter Resins and Related Compounds" abstract & Agricultural and Biological Chemistry, vol. 49, No. 2, 1985, pp. 399–404, ISSN 0002–1369.

(List continued on next page.)

Primary Examiner—Peter A. Hruskoci
(74) Attorney, Agent, or Firm—Joanne Rossi (57) ABSTRACT

Methods of inhibiting the growth of organisms in aqueous systems such as papermaking systems, cooling systems and process waters of various types, comprises adding to the aqueous system a hop acid. Compositions comprising hop acids and papermaking suspensions or slurries, and/or additives, such as paper making additives, are also provided.

37 Claims, 2 Drawing Sheets

FOREIGN PATENT DOCUMENTS

| WO | 98/11883 | 3/1998 |
|----|----------|--------|
| WO | 00 52212 | 9/2000 |
| WO | 00 53814 | 9/2000 |
| WO | 01 06877 | 1/2001 |
| WO | 01 66471 | 9/2001 |
| WO | 02 05637 | 1/2002 |

OTHER PUBLICATIONS

English Language Abstract of JP 9–67250.

"Antimicrobial Activity of the Semisynthetic Compound, Hexahydrocolupulone", T.E. Stephan et al., *Journal of Antimicrobial Chemotherapy* (1998) 41, 519–522.

"Investigation of Hop and Beer Bitter Acids by Coupling of High–performance Liquid Chromatography to Nuclear Magnetic Resonance Spectroscopy", K. Pusecker et al., *Journal of Chromatography a*, 836 (1999), 245–252.

S. S. Block, Ph. D., *Disinfection, Sterilization, and Preservation, Fourth Edition* (1991), Table 56–2.

"Hydrohop", *Material Safety Data Sheet* (2 pgs) Jun. 25, 1999.

* cited by examiner

METHODS OF USING HOP ACIDS TO CONTROL ORGANISMS

BACKGROUND OF THE INVENTION

1. Field of the Invention

This invention relates to the control of organisms, such as microorganisms, and in particular the inhibition of such organisms by employing hop acids to inhibit the growth of such organisms and/or kill such organisms. By way of illustration only, the invention has particular utility in aqueous systems, such as papermaking systems and process water systems, in particular systems that involve circulating and/or recirculating water systems, such as cooling water systems, etc.

2. Background of the Invention and Related Art

The control of organisms, and microorganisms in particular, has been a continuing and troublesome problem in aqueous systems, such as systems that involve circulating and/or recirculating water systems, such as such as papermaking systems and process water systems, cooling water systems, etc. Such microorganisms cause biofouling, such as deposits of microorganisms or products (such as metabolic products) of microorganisms that cause the formation of deposits such as films, mats and other deposits which can result in plugging of pores, reduced flow, reduced heat exchange rates, clogging, etc.

Slime formation, deposit formation and the formation of filamentous bacteria have been of particular concern, for example.

By way of non-limiting example only, filamentous bacteria (for example, *Sphaerotilus natans*) are often the cause of deposits on paper machines and fouling in cooling systems. Many types of filamentous bacteria grow on submerged surfaces in single chains within structures referred to as "sheaths." Sheaths are considered to be a protective structure, and as such, the structure promotes the survival of the organism. For example, the sheath structure is thought to protect the organism from biocides, because, for example, getting the biocide into the protective structure poses a problem. Filamentous bacterial growth on submerged surfaces in paper process streams can contribute to the formation of large deposits consisting of cells and inert materials (particulates, fines, fiber, etc.) that become enmeshed in the filaments. Long "stringers" of the filamentous bacteria as well as large clumps of deposits can become dislodged and cause problems such as holes, other defects, and breaks in the paper. This, therefore, can cause significant increases in the cost of producing paper. Filamentous bacteria also cause problems in cooling towers. Submerged surfaces fouled with filamentous and other types of bacteria cause a reduction in the efficiency of heat transfer, in cooling systems for example, as well as other problems resulting from large amounts of biomass becoming dislodged and circulating within an industrial setting.

The control of such microorganisms is even more difficult in view of the fact that many of the microorganisms which are the cause of such problems are resistant to attempts to control them, such as by inhibiting their growth and/or killing them. For example, microorgansims that pose problems in aqueous industrial systems, such as process waters and papermaking systems, are resistant to a broad spectrum of conditions and materials, and thus are able to remain viable in a wide variety of such conditions. Therefore, biocides have been employed in efforts to control such microorganisms. However, conventional biocides are expensive, are not sufficiently environmentally friendly, exhibit an undesirably broad spectrum of activity (i.e., they are not targeted to the specific microorganisms desired to be killed), must be employed in relatively large concentrations, and/or can be harmful and/or dangerous and/or even toxic to humans. Moreover, in aqueous systems or media in which the control of organisms is desired, the compatibility of the compositions and methods employed are also a consideration. Accordingly, a biocide which is effective with regard to the foregoing and which does not exhibit the mentioned disadvantages is desired.

With respect to all of the foregoing, there has been a continuing need for improvement.

It is known in the brewing industry that some hop acids can inhibit the growth of microorganisms that can cause spoilage in beer. For example, U.S. Pat. No. 5,082,975 discloses that the hop acid, hexahydrolupulone, can inhibit the growth of certain Lactobacillus. This patent further discloses that there has been speculation that hops may have helped control brew house bacterial infections due to the presence of hop acids in the wort and beer. However, since the hop beta acids are not found in beer, such control, if it indeed existed, was thought to have been due to the hop alpha acids and iso-alpha acids. Beta acids are known to be highly unstable, being oxidized in the boiling wort to bitter hulupones and by themselves to deteriorate in a matter of days or hours after crystallization. This lack of stability is now shown to be overcome by conversion to hexahydrolupulone (hexahydro beta acids). There is a vast excess of lupulone available as a result of being discarded in the brewing process, making it a potentially inexpensive raw material. U.S. Pat. No. 4,918,240 is a related patent to U.S. Pat. No. 5,082,975. Each of these patents is hereby incorporated by reference as though set forth in full herein.

U.S. Pat. No. 5,455,038 discloses that the hop acids, tetrahydroisohummulone and hexahydrocolupulone ($\alpha$ and $\beta$ hops, respectively), a product of the brewing industry, have been identified as compounds that can inhibit food born pathogens from the genera Listeria, Staphylococcus, Bacillus, and Clostridium. In addition, U.S. Pat. No. 5,286,506 discloses that solid food products can be protected from food pathogens, including *Listeria monocytogenes*, by incorporating beta-acids, which are extracted from hops, into such food products. U.S. Pat. No. 5,455,038 discloses the inhibition of Listeria with $\alpha$ and $\beta$ hop acids. Each of these patents is hereby incorporated by reference as though set forth in full herein.

Derivatives of the $\beta$-hydrogenated lupulones can inhibit or kill cancer cells (WO 97/31630 and WO 98/11883) as well as antibiotic resistant strains of *Staphylococcus aureus, Mycobacterium tuberculosis,* and *Mycobacterium avian* Complex or enterococcus ("Antimicrobial activity of the Semisynthetic Compound, Hexahydrocolupolone", Stephan et al., *Journal of Antimicrobial Chemotherapy* (1998) 41, 519–522). Each of these documents is hereby incorporated by reference as though set forth in full herein. Additionally, $\alpha$ and $\beta$ hop acids have been identified as a therapeutic agent for methicillin resistant *Staphylococcus aureus* (Japanese Patent document JP 9067250). This document is hereby incorporated by reference as though set forth in full herein.

U.S. Pat. No. 5,370,863 discloses that oral care compositions containing hop acids or their salts are effective in inhibiting Gram positive bacteria, including *Streptococcus mutans*, which can cause plaque or periodontal disease, which document is hereby incorporated by reference as though set forth in full herein. A representative composition is a toothpaste containing tetrahydroisohumulone.

Hop acids have been considered to be selective to Gram-positive bacteria. See, for example, WO 98/11883, incorporated by reference above.

SUMMARY OF THE INVENTION

The invention provides a method of controlling organisms, such as microorganisms, particularly bacteria, in aqueous systems or media, such as papermaking systems and process water systems, in particular systems that involve circulating and/or recirculating water systems, such as cooling water systems, etc., which method employs materials which are readily available from renewable resources and which are also effective.

The invention provides a method of controlling such organisms in such aqueous systems which method employs materials which are relatively inexpensive.

The invention provides a method of controlling such organisms in such aqueous systems which method is effective against a wide variety of microorganisms but which are also targeted to the microorganisms which affect such aqueous systems.

The invention provides a method of inhibiting the growth of organisms in an aqueous system selected from a papermaking system, a cooling system or a process water which process water does not contact a final product; or combinations thereof, comprising adding to the aqueous system a hop acid.

Preferably, the hop acid comprises a member selected from α or β hop acids, and mixtures thereof.

In preferred embodiments, the method comprises adding a hop acid selected from one or more of a compound of Formula (I):

(I)

wherein "----" represents an optional double bond;

$R_1$ comprises a member selected from OH; and saturated, or unsaturated (containing from about 1 to about 5 double bonds), straight- or branched-chain alkyl or alkenyl of from about 1 to about 20 C atoms, more preferably from about 1 to about 10 C atoms and more preferably from about 1 to about 5 C atoms;

$R_2$ comprises a member selected from —OH; =O; —SH; =S; and saturated, or unsaturated (containing from about 1 to about 5 double bonds), straight- or branched-chain alkyl or alkenyl of from about 1 to about 20 C atoms, more preferably from about 1 to about 10 C atoms and more preferably from about 1 to about 5 C atoms;

$R_3$ comprises a member selected from —OH; =O; —SH and =S; and —OOR, wherein R comprises a member selected from H and $C_nH_{2n-1}$, where n is an integer of from about 2 to about 10, more preferably from about 2 to about 7, and more preferably from about 2 to about 5;

$R_4$ comprises a member selected from saturated or unsaturated (containing from about 1 to about 5 double bonds), straight- or branched-chain alkyl or alkenyl of from about 1 to about 20 C atoms, more preferably from about 1 to about 10 C atoms, and more preferably from about 1 to about 5 C atoms; a ketone of from about 1 to about 20 carbon atoms, more preferably from about 1 to about 10 carbon atoms, and more preferably from about 1 to about 4 carbon atoms, an aldehyde of the general formula C(O)H, or a ketone of the general formula $C(O)C_nH_{2n+1}$, where n is an integer of from about 2 to about 10, more preferably from about 2 to about 7, and more preferably from about 2 to about 5; and —OOR, wherein R comprises a member selected from $C_nH_{2n+1}$ wherein n is as defined previously, and H; and/or Formula (II):

(II)

wherein $R_5$ comprises a ketone of the general formula $C(O)C_nH_{2n-1}$, where n is an integer of from about 2 to about 10, more preferably from about 2 to about 7, and more preferably from about 2 to about 5;

$R_6$ comprises a member selected from —OH, —SH, and —OOR, wherein R comprises a member selected from $C_nH_{2n+1}$ where n is an integer of from about 2 to about 10, more preferably from about 2 to about 7, and more preferably from about 2 to about 5; and H; and $R_7$ comprises a member selected from saturated or unsaturated (containing from about 1 to about 5 double bonds), straight- or branched-chain alkyl or alkenyl of from about 1 to about 20 C atoms, more preferably from about 1 to about 10 C atoms, and more preferably from about 1 to about 5 C atoms;

$R_8$ comprises member selected from saturated or unsaturated (containing from about 1 to about 5 double bonds), straight- or branched-chain alkyl or alkenyl of from about 1 to about 20 C atoms, more preferably from about 1 to about 10 C atoms, and more preferably from about 1 to about 5 C atoms; a ketone of from about 1 to about 20 carbon atoms, more preferably from about 1 to about 10 carbon atoms, and more preferably from about 1 to about 4 carbon atoms, an aldehyde of the general formula C(O)H, or a ketone of the general formula $C(O)C_nH_{2n+1}$, where n is an integer of from about 2 to about 10, more preferably from about 2 to about 7, and more preferably about 5; and/or Formula (III):

(III)

wherein $R_9$ comprises a saturated, or unsaturated (containing from about 1 to about 5 double bonds), straight- or branched-chain alkyl or alkenyl of from about 1 to about 20 C atoms, more preferably from about 1 to about 10 C atoms and more preferably from about 1 to about 5 C atoms; and $R_{10}$ comprises a member selected from a ketone of from about 1 to about 20 carbon atoms, more preferably from about 1 to about 10 carbon atoms, and more preferably from about 1 to about 4 carbon atoms, an aldehyde of the general formula C(O)H or a ketone of the general formula $C(O)C_nH_{2n-1}$, where n is an integer of from about 2 to about 10, more preferably from about 2 to about 7, and more preferably from about 2 to about 5; and/or Formula (IV):

(IV)

wherein $R_{11}$ comprises a saturated, or unsaturated (containing from about 1 to about 5 double bonds), straight- or branched-chain alkyl or alkenyl of from about 1 to about 20 C atoms, more preferably from about 1 to about 10 C atoms and more preferably from about 1 to about 5 C atoms; and $R_{12}$ comprises a member selected from a ketone of from about 1 to about 20 carbon atoms, more preferably from about 1 to about 10 carbon atoms, and more preferably from about 1 to about 4 carbon atoms, an aldehyde of the general formula C(O)H, or a ketone of the C(O) $C_nH_{2n-1}$, where n is an integer of from about 2 to about 10, more preferably from about 2 to about 7, and more preferably from about 2 to about 5.

Preferably $R_4$ comprises a substituent of the formula wherein $R_{13}$ comprises a $C_3$–$C_8$ alkyl group.

Preferably $R_{13}$ comprises a member selected from —$CH_2CH(CH_3)_2$; —$CH(CH_3)_2$; and —$CH(CH_3)_2CH_2CH_3$.

Preferably the method comprises adding a hop acid which comprises a member selected from hexahydrolupulone; hexahydrocolupulone; hexahydroadlupulone, and mixtures thereof.

Preferably the hop acid comprises hexahydrocolupulone.

Preferably $R_8$ comprises a substituent of the formula wherein $R_{14}$ comprises a $C_3$–$C_8$ alkyl group.

Preferably $R_{14}$ comprises a member selected from $CH_2CH(CH_3)_2$; —$CH(CH_3)_2$; —$(CH_2)_2CH(CH_3)_2$; —$CH(CH_3)_2$ $CH_2CH_3$. and mixtures thereof.

Preferably the hop acid comprises tetrahydroisohumulone.

The organism can comprise a microorganism selected from Gram-negative bacteria, Gram-positive bacteria, and mixtures thereof.

The microorganism can comprise a member selected from *Sphaerotilus natans, Clostridium butyricum, Pseudomonas aeruginosa, Curtobacterium flaccumfaciens, Burkholderia cepacia, Pseudomonas glathi, Bacillus cereus, Bacillus maroccanus, Bacillus licheniformis, Bacillus sphaericus, Bacillus subtilis*, and mixtures thereof.

The microorganism can comprise a Gram-negative bacteria.

The microorganism can comprise a member selected from Altermonas, Aquaspirillum, Campylobacter, Helicobacter, Acinetobacter, Agrobacterium, Alcaligenes, Alteromonas, Flavobacterium, Pseudomonas, Xanthomonas, Mycoplasma, Methanococcus mixtures thereof.

The microorganism can comprise a Gram-positive bacteria.

The microorganism can comprise a member selected from Bacillus, Enterococcus, Planococcus, Staphylococcus, Streptococcus, Clostridium, Lactobacillus, Listeria, Actinomyces, Arthrobacter, Corynebacterium, Curtobacterium, Norcardia, Actinoplanes, Mycobacterium and mixtures thereof. mixtures thereof.

The aqueous system can comprise a papermaking system.

The aqueous system can comprise a process water.

The aqueous system can comprise a cooling system.

The hop acid preferably is present in an amount of from about 0.001 to about 1,000 ppm.

The hop acid is preferably present in an amount of from about 0.1 to about 250 ppm.

The hop acid is preferably present in an amount of from about 0.1 to about 100 ppm.

The hop acid is preferably added with a freezing point depressant.

The invention also comprises a method of inhibiting the growth of organisms in a papermaking system, comprising adding to the papermaking system a hop acid in accordance with any of the foregoing definitions.

The invention also provides a composition comprising a hop acid in accordance with any of the foregoing definitions and a member selected from a papermaking suspension, a defoamer, an alum, an adhesive, a paper mill coating, a pigment slurry, a starch, a pitch control agent, a scale control agent, a sizing agent, and mixtures thereof.

Preferably, the papermaking suspension comprises a member selected from refined or unrefined furnish stock; refined or unrefined pulp; paper making furnish, and combinations thereof.

The invention also provides a cellulosic product comprising a member selected from paper and paper board.

The paper can comprise a member selected from stationery paper, paper towel and tissue paper.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF PREFERRED EMBODIMENTS

The present invention is based on the discovery that hop acids can be employed to control organisms such as by inhibiting the growth of and/or killing organisms including both Gram-positive and Gram-negative microorganisms. As used herein the terms "control of organisms" and "inhibition of organisms" is intended to include either or both of the inhibition of the growth of organisms and killing organisms, and these terms should be interpreted as being interchangeable herein.

The invention is particularly directed to the control of organisms in aqueous systems such as papermaking systems and process water such as cooling water, as well as any other aqueous system. As used herein "aqueous systems" and "aqueous media" are intended include any part of the aqueous system in question and to include the addition of hop acid at any point within or external to the system, especially in cases which result in a hop acid being present in a portion of the aqueous system. Thus, the invention is expressly intended to cover situations where the hop acid is added upstream of and/or downstream of and/or directly and/or indirectly to the aqueous system in question. Moreover, the terms "aqueous systems" and "aqueous media" are intended to cover any situation or environment in which water is present, including slurries and solutions as illustrative, non-limiting examples.

The methods of the invention are useful in treating any aqueous system or media in which it may be desired to inhibit the growth of and/or kill organisms such as microorganisms. As discussed elsewhere herein, in some embodiments, the processes of the invention involve adding hop acids to aqueous systems which may come into direct contact with final product, such as aqueous systems associated with papermaking. In other embodiments, the processes of the invention involve adding hop acids to aqueous systems which do not directly contact final product. Illustrative, non-limiting examples of aqueous systems which do not directly contact final product include recirculating process waters such as cooling waters which may be separated by a final product by a barrier such as a heat exchanger, etc.

Thus, "aqueous system" refers to industrial aqueous systems in addition to papermaking systems and are intended to embrace any such aqueous system wherein the water of the system, such as a process water, does not come into contact with the final product. Non-limiting examples include cooling water systems, such as internal combustion engine cooling systems, power plant cooling systems; heat exchangers, including radiator coolants, etc.; aqueous systems used in humidifiers; aqueous systems used in heating, ventilating and air conditioning systems; swimming pool water; water used in spas; metal working fluids; petroleum production fluids including drilling muds; paint formulation; disinfectants and sanitizers; plastics processing systems; mixtures of the foregoing; and any other aqueous systems. Methods of the invention control organisms in such systems by adding a hop acid to the papermaking system or other aqueous systems.

Any hop acid may be employed in the methods of the invention. It has been found that α and/or β hop acids are particularly suitable, such as those of Formula (I), (II) (III) and (IV), above.

As used herein, whenever reference is made to a compound or component, unless otherwise stated, it includes the individual compound or component by itself as well as mixtures of the compound or component, unless otherwise excluded. Thus, for example, reference to hop acids includes the occurrence of a single hop acid and to mixtures of various hop acids and mixtures with various other materials.

Further, when an amount, concentration, or other value or parameter, is given as a list of upper preferable values and lower preferable values, this is to be understood as specifically disclosing all ranges formed from any pair of an upper preferred value and a lower preferred value, regardless whether ranges are separately disclosed.

It is specifically contemplated that mixtures of compounds of Formula (I) with other compounds of Formula (I) and mixtures of compounds of Formula (II) with other compounds of Formula (II), and mixtures of compounds of Formula (III) with other compounds of Formula (III), and mixtures of compounds of Formula (IV) with other compounds of Formula (IV), as well as mixtures of compounds of Formulae (I), (II), (III) (IV), in any combination of one or more of such compounds of Formulae (I), (II), (III) or (IV), can also be employed. Compounds of Formulae (I) and (III) are predominately β hop acids (but also can include some α hop acids) and compounds of Formula (II) are predominately α hop acids (but also can include some β hop acids).

Non-limiting examples of α hop acids include: humulone, isohumulone; cohumulone; adhumulone; tetrahydroisohumulone; tetrahydrodeoxyhumulone.

Non-limiting examples of β hop acids include lupulone; colupulone; hexahydrocolupoulone; and hexahydrolupulone.

Especially preferred hop acids of Formula (I) include those wherein $R_4$ comprises wherein $R_{13}$ comprises a member selected from ($C_3$–$C_8$) alkyl, such as —$CH_2CH(CH_3)_2$; —$CH(CH_3)_2$; and —$CH(CH_3)_2CH_2CH_3$. Exemplary compounds are disclosed in WO 98/11883, which is hereby incorporated by reference herein in its entirety for its disclosure of such compounds and include hexahydrolupulone (R=—$CH_2CH(CH_3)_2$); hexahydrocolupoulone or "HHC" (R=$CH(CH_3)_2$); and hexahydroadlupulone (R=$CH(CH_3)_2CH_2CH_3$). Hexahydrocolupulone or "HHC" is a particularly preferred compound of Formula (I).

Especially preferred hop acids of Formula (II) include those wherein $R_8$ comprises wherein $R_{14}$ is selected from ($C_3$–$C_8$) alkyl, such as —$CH_2CH(CH_3)_2$; —$CH(CH_3)_2$; —$CH_2)_2CH(CH_3)_2$; and —$CH(CH_3)_2$ $CH_2CH_3$.

Particularly preferred compounds of Formula (II) include those wherein R comprises —$(CH_2)_2CH(CH_3)_2$, such as tetrahydroisohumulone. Of these, tetrahydroisohumulone is particularly preferred.

Particularly preferred compounds of Formula (III) include cohumulone.

Particularly preferred compounds of Formula (IV) include tetrahydrodeoxyhumulone as disclosed in U.S. Pat. No. 4,918,240, which document is hereby incorporated by reference as though set forth in full herein for this disclosure as well.

Further elucidation of the structure and nomenclature of many of the foregoing compounds of Formulae (I) and (II) may be found in "Investigation of Hop and Beer Bitter Acids by Coupling of High-performance Liquid Chromatography to Nuclear Magnetic Resonance Spectroscopy", Pusecker et al., *Journal of Chromatography a,* 836 (1999), 245–252, which is hereby incorporated by reference as though set forth in full herein.

In general, compounds of the foregoing Formulae I–IV which are water soluble are preferred. Also in general, the fewer the number of carbon atoms in the "R" group substituents denoted with "n" above, the more soluble the resulting compound. In preferred embodiments, n is an integer of from about 1 to about 10, more preferably from about 2 to about 7 and more preferably about 2 to about 5.

Hop acids may be isolated and prepared in any suitable way by those of ordinary skill in the art, such as those disclosed in the documents incorporated by reference above, which are also incorporated by reference for their disclosures of how to prepare such hop acids. Among those incorporated by reference, WO 98/11883, U.S. Pat. No. 4,918,240 and U.S. Pat. No. 5,082,975 are instructive. Hop acids useful in accordance with the present invention may also be prepared in accordance with the disclosure of U.S. Pat. No. 4,844,939 to TODD, Jr., which document, as well as all documents cited therein, is hereby incorporated by reference as though set forth in full herein for their disclosure of how to prepare hop acids. For example, this patent discloses that refined, preisomerized hop extracts are available in the trade as solutions made according to various U.S. patents, such as U.S. Pat. Nos. 3,558,326, 3,798,332, 3,965,188 (Westerman et al); U.S. Pat. Nos. 3,949,092 and 3,973,052 (Mitchell); and U.S. Pat. Nos. 3,486,906 and 4,002,683 (Todd), all of which documents are hereby incorporated by reference as though set forth in full herein. To overcome the disadvantage of using artificial, organic solvents, the use of liquid and supercritical carbon dioxide for the extraction of hops has been employed. This art is described in Kruger (Monatsschrift fur Brauerei, 33, Nr. 3), which document is hereby incorporated by reference as though set forth in full herein. Moreover, methods for the isomerization and separation of the constituents of carbon dioxide hop extracts can also employ organic solvents and/or adsorption/extraction processes (Lance U.S. Pat. No. 4,395,431, which document is hereby incorporated by reference as though set forth in full herein or Mueller, Deutsche Auslegeschrift No. 2920765 which document is hereby incorporated by reference as though set forth in full herein), or "salt out" impurities (Laws U.S. Pat. No. 4,298,626 which document is hereby incorporated by reference as though set forth in full herein), or remove them by filtration using large amounts of adsorbent in dilute solution (Baker U.S. Pat. No. 4,247,483 which document is hereby incorporated by reference as though set forth in full herein), all of the foregoing being cited in U.S. Pat. No. 4,844,939 to TODD, incorporated by reference above.

The hop acids may preferably be employed in the form of an aqueous solution, such as disclosed in WO 98/11883, U.S. Pat. Nos. 4,918,240 and 5,082,975 and the solutions can be prepared as disclosed therein, which documents are again specifically incorporated by reference herein for this purpose.

Suitable hop acids are commercially available in the form of an aqueous solution under the trade name "HYDROHOPS" available from Watertown Hops Company, 1224 American Way, Watertown, Wis., 53094.

It has been found that the aqueous solution under the trade name "HYDROHOPS" can be employed directly by being directly added to the aqueous system to be treated without the need for further formulation.

Propylene glycol, glycerine, similar stable alcohols and polyols, or mixtures thereof with or without water, may be substituted for the water of the aqueous solution.

The solubility of the hop acids employed in the present invention can be affected by temperature. For example, the hop acids may be subject to crystallization at temperatures lower than room temperature. Therefore, it has been found particularly advantageous to employ one or more freezing point depressive agents. The agents are preferably employed in any amount effective to lower the freezing point of the composition so as to inhibit cloudiness and/or crystallization of hop acid. Any freezing point depressive agent may employed and may be readily selected by those of ordinary skill in the art. Examples include:

Glycerol (glycerine); polyglycerols such as diglycerol, triglycerol, tetraglycerol, pentaglycerol, hexaglycerol, and higher oligomers of glycerol;

Glycols, such as ethylene glycol, diethylene glycol, propylene glycol, dipropylene glycol, tripropylene glycol, and higher oligomers of glycols;

Polyglycol triols selected from glycerol propoxylate, glycerol ethoxylate, and mixtures thereof;

Monohydric alcohols, which can range for example, from methyl through $C_{50}$ alcohols, more preferably $C_6$–$C_{36}$, and may include, for example, methanol, ethanol, isopropanol, butanol, isobutanol, amyl alcohol, isoamyl alcohol, hexanol, isohexanol, heptanol, n-octanol, 2-ethylhexanol, iso-octanol, n-nonanol, isononyl alcohol, n-decanol, isodecanol, n-lauryl alcohol, tridecanol, n-myristyl alcohol, n-cetyl alcohol, isocetyl alcohol, n-stearyl alcohol, isostearyl alcohol, octyldodecanol, archidyl alcohol, capryl alcohol, oleyl alcohol, alcohols up through $C_{50}$, more preferably up through $C_{36}$, ethoxylated and/or propoxylated versions of the above-described alcohols, phenoxyethanols, and ethoxylated and/or propoxylated versions of the above-described alcohols, phenoxyethanols, and ethoxylated and/or propoxylated nonyl phenols (numerous additional alcohols, including monohydric alcohols being readily selectable by those of ordinary skill in the art); and other freezing point depressive actives, such as monohydric alcohol diester (used in the cosmetic and personal care industries), Triclosan (2,4,4'-trichloro-2'-hydroxyl diphenyl ether), alkyl glycol ethers (dipropylene glycol methyl ether), salts (organic and inorganic) polyethylene glycols, alkyl carbitols, peptides ("antifreeze peptides"), glycopeptides ("antifreeze glycopeptides"), alkyl amines, etc.

In accordance with the invention, hop acids may be employed in any amount effective to control the organism, as by inhibiting the growth of and/or killing, organisms. In general, for the aqueous systems referenced herein, the hop acid should be employed in amounts of from about 0.001 to about 1,000 ppm, preferably from about 0.1 to about 250 ppm, and more preferably from about 0.1 to about 100 ppm, based on amount of active ingredient (hop acid) in the aqueous system in question on an as is basis.

It has surprisingly been found that the invention is suitable for controlling a wide variety of organisms, including microorganisms such as Gram-negative as well as Gram-positive bacteria. It is particularly surprising that hop acids can be employed to control Gram-negative microorgansims. Other microorganisms can be inhibited by the invention as well, including dinoflagellattes, microalgae, microfungi, bacteria, protozoans or mixtures thereof. The invention is particularly effective in controlling the vegetative form of microorganisms.

Examples of Gram-negative microorganisms which can be inhibited by the methods of the invention include Genus Altermonas, Genus Aquaspirillum, Genus Campylobacter, Genus Helicobacter, Genus Acinetobacter, Genus Agrobacterium, Genus Alcaligenes, Alteromonas, Genus Flavobacterium, Genus Pseudomonas, Genus Xanthomonas, Genus Mycoplasma, Genus Methanococcus, and mixtures thereof.

Examples of Gram-positive microorganisms which can be inhibited by the methods of the invention include Genus Bacillus, Genus Enterococcus, Genus Planococcus, Genus Staphylococcus, Genus Streptococcus, Genus Clostridium, Genus Lactobacillus, Genus Listeria, Genus Actinomyces, Genus Arthrobacter, Genus Corynebacterium, Genus Curtobacterium, Genus Norcardia, Genus Actinoplanes, Genus Mycobacterium and mixtures thereof.

The invention is also effective against Family Enterobacteriaceae, including Genus Escherichia, Genus Enterobacter, Genus Klebsiella, and mixtures thereof, as well as Family Vibronacea, including Genus Aeromonas, Genus Vibrio and mixtures thereof.

The invention is also effective against other bacteria, including Genus Desulfovibrio, Genus Thiobacterium and mixtures thereof.

Other microorganisms against which the invention is effective, as well as species of the foregoing may be found in *Bergey's Manual of Determinative Bacteriology*, Holt et al., Williams & Wilkins, Ninth Edition (1994) which document is hereby incorporated by reference as though set forth in full herein. The sections: Group 2 (including page 39), Group 3 (including page 71), Group 5 (including page 175), Group 12 (including page 427), Group 14 (including page 477), Group 17 (including page 527), and Group 18 (including page 559) are also hereby incorporated by reference as though set forth in full herein for their more specific disclosure of such microorganisms.

Methods of the invention have been found particularly effective in controlling microorganisms selected from *Sphaerotilus natans, Clostridium butyricum, Pseudomonas aeruginosa, Curtobacterium flaccumfaciens, Burkholderia cepacia, Pseudomonas glathi, Bacillus cereus, Bacillus maroccanus, Bacillus lichen iformis, Bacillus sphaericus, Bacillus subtilis*, and mixtures thereof.

Whether inhibition of growth or killing of a microorganism has occurred, and the extent to which it has occurred can be measured by those of ordinary skill in the art, such as in accordance with the Examples below.

In accordance with the methods of the invention, hop acids may be added to the aqueous system to be treated in any manner. In many cases the method of the invention may be conducted by simply adding a commercially available solution of hop acids, such as HYDROHOPS directly to the aqueous system to be treated. The hop acid may also be added after being diluted or added to other media to form an admixture or solution, which admixture or solution may then be added to the aqueous system to be treated. Thus, the hop acid may be added by being added as a component to additives for papermaking or other aqueous systems, the formulation of which additives is otherwise well known to those of ordinary skill in the art.

Treatment of Papermaking Systems

The invention may be applied to any papermaking system at any point in the system and in any manner where additives are typically employed and in any manner that additives used in the paper industry are employed. Solutions, such as aqueous solutions of hop acids may be employed directly and/or indirectly, or in admixture with any papermaking additive, such as those papermaking additives discussed herein.

Non-limiting examples of suitable aspects for addition include:

Refined or unrefined furnish stock in stock tanks.

Pulp refining conducted in a refiner.

Refined pulp stored, ready for use in stock chests.

Paper making furnish drawn from stock chests.

The flow box, the point at which the paper making furnish flows at a controlled rate onto the fourdrinier wire.

Or any combination of the foregoing, upstream of any of the foregoing locations, or any point in between such locations, or any other suitable location, or combination of locations, concurrently or at different times.

Preferably, hop acids in accordance with the invention may be employed in the amounts discussed above.

When added to a papermaking composition such as a papermaking additive or papermaking pulp or slurry, the hop acid can become a component of the resultant product. Thus, the invention also provides cellulosic products such as paper and paper products comprising hop acids. The presence of hop acids in cellulosic products including paper and paper products provides advantages of effectively controlling organisms in the aqueous systems associated with the production of such products, while not posing safety, toxicity or related concerns, and/or adverse physiological reactions. This is of particular significance with respect to cellulosic products comprising members selected from stationery paper, paper towel and tissue paper.

Treatment of Other Process Waters

The invention may be applied to any process water system at any point in the system and in any manner where additives are typically employed and in any manner that additives used in such industries are employed. Non-limiting examples of suitable aspects for addition include addition at the normal fill opening of the system, incorporation with or as part of the original liquid added to the system, etc.

Any combination of the foregoing may be employed.

Compositions

As can be seen, the invention also comprises composition aspects.

Thus, as non-limiting examples, the invention also provides a composition comprising a hop acid and an aqueous medium selected from a papermaking systems and other aqueous systems such as emulsions, adhesives, process waters, including cooling water systems, such as internal combustion engine cooling systems, power plant cooling systems; heat exchangers, including radiator coolants, etc.; aqueous systems used in humidifiers; aqueous systems used in heating, ventilating and air conditioning systems; swimming pool water; water used in spas; metal working fluids; petroleum production fluids including drilling muds; paint formulation; disinfectants and sanitizers; plastics; mixtures of the foregoing; and any other aqueous systems.

Additional exemplary applications for such compositions are provided in *Disinfection, Sterilization, and Preservation*, Fourth Edition, Block, Lea & Febiger (1991), which is hereby incorporated by reference as though set forth in full herein, for its disclosure of such applications. Table 56-2 of this document is also expressly incorporated by reference herein in its entirety.

The invention further provides a composition compositions which are preserved for later addition to aqueous systems, such as additives for paper making and water treatment additives. Thus, the invention also comprises compositions comprising a hop acid and a paper making additive selected from defoamers, alum, adhesives, paper mill coatings, pigment slurries, starches, pitch control agents, scale control products, sizing agents (including alkyl ketene dimer sizing agents (AKD's), and mixtures thereof. Papermaking compositions in accordance with the invention comprise Non-limiting examples of suitable composition aspects:

Refined or unrefined furnish stock in stock tanks.

Pulp such as that in a refiner.

Refined pulp stored, ready for use in stock chests.

Paper making furnish drawn from stock chests.

The flow box, the point at which the paper making furnish flows at a controlled rate onto the fourdrinier wire.

Or any combination of the foregoing, upstream of any of the foregoing locations, or any point in between such locations, or any other suitable location, or combination of locations, concurrently or at different times.

Details and optimization of routine components, formulations, and use considerations can be found, for example, in *Pulp and Paper, Chemistry and Chemical Technology*, Casey, James P. (editor), J. Wiley, 3d. edition (1980), the entire disclosure of which is hereby incorporated by reference, as though set forth in full herein for this purpose.

Without further elaboration, it is believed that one skilled in the art can, using the preceding description, utilize the present invention to its fullest extent.

The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

Example 1

Control of *S. natans*

This example illustrates that a derivative of a naturally occurring compound in hops can control the growth of *S. natans*, a filamentous organism. The results of adding selected concentrations of hop acids to cultures of *S. natans* are presented below. In those studies, individual flasks containing a dilute culture medium (e.g., CYG broth, described in more detail below) were inoculated with different strains of *S. natans* (ATCC 15291 and ATCC 29329), and selected concentrations of hop acid (HYDROHOPS from Watertown Hops, diluted to 10, 25, and 50 ppm tetrahydroisohumulone). The cultures were incubated and, after 48 and 96 hours, the flasks were agitated, and a 1 ml sample removed for ATP measurement. The difference between untreated controls and treated cultures yielded the percent inhibition. Specific protocol included the following: *S. natans* (ATCC cultures 15291, 29329, and 13925) were grown on CYG broth which had the following composition: 0.5 g/l casitone, 1.0 g/l glycerol, and 0.1 g/l yeast extract. *S. natans* strains were grown in 50 ml culture volumes in shake flasks on an orbital shaker at room temperature. Experiments were initiated by inoculating tests flasks with equal amounts of *S. natans* taken from 48 hour to 72 hour old broth cultures. Selected concentrations of the active were added to flasks containing *S. natans*. The control used in all experiments were untreated. The effect of hop acid on *S. natans* was quantitated using ATP measurements. ATP analysis was conducted using reagents and luminometer from Biotrace Ltd (Bridgend, U. K.). ATP extractions and measurements were carried out as follows:

1. Test cultures are repeatedly mixed with a 10 ml pipet to break up flocs and yield a uniform suspension.
2. 100 microliters of culture is combined with 100 microliters of extractant in a test tube. The tube is then shaken and let stand at room temperature for 1 minute.
3. 100 microliters of luciferase enzyme is added to the mixture, shaken and placed in the luminometer. A reading (relative light units—rlu), corresponding to the amount of ATP extracted is recorded. All data were generated using replicate extractions.

Data Analyses:

The rlu readings for each treated flask were normalized with the control reading to yield a percent inhibition of growth.

Figure 1:
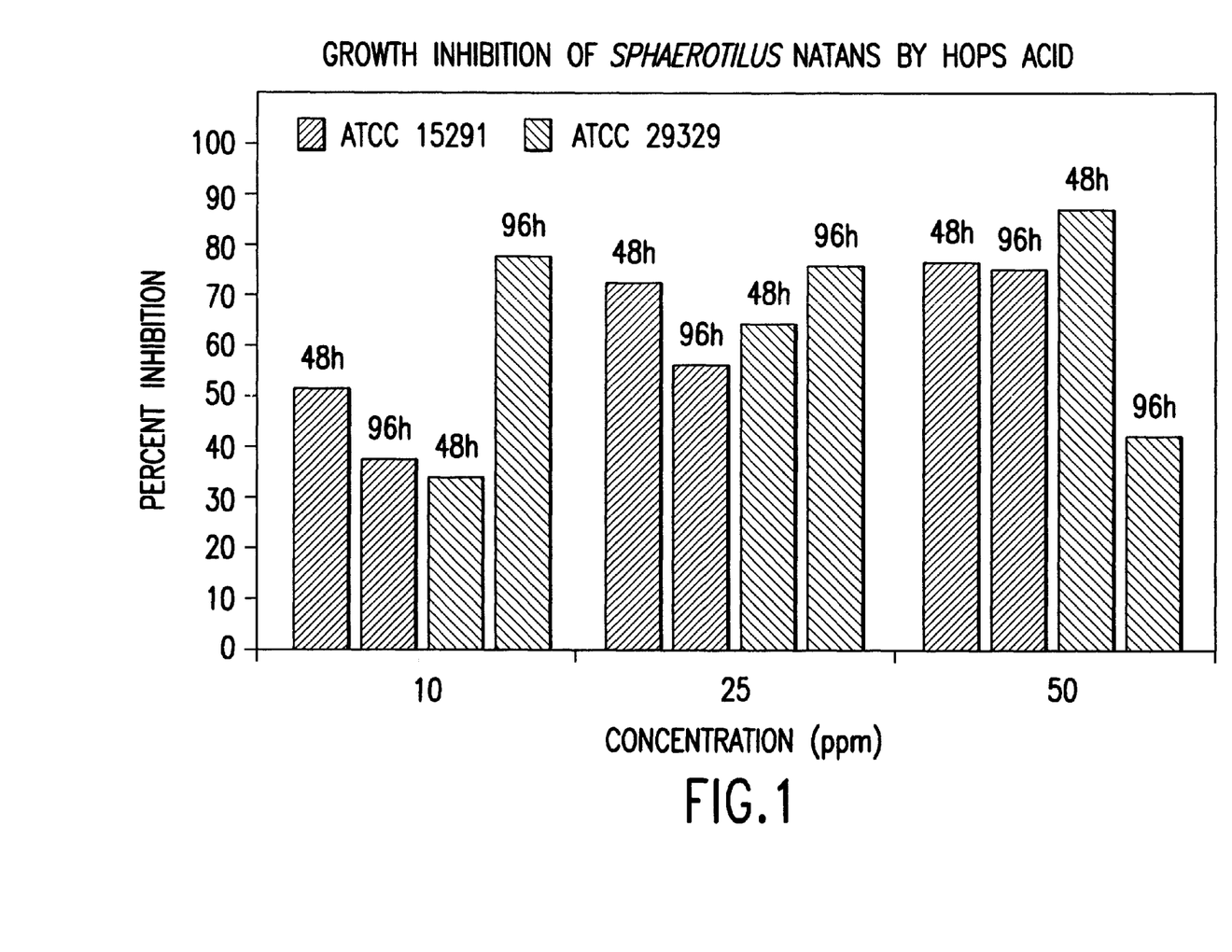
FIG. 1 illustrates the growth inhibition of *S. natans* by hop acid in accordance with the following examples.

The graph in FIG. 1 indicates that the $I_{50}$ value (the concentration of active needed to inhibit 50% of the population) for both strains of microorganisms is ca. 10 ppm.

Example 2

Inhibition of *Clostridium butyricum*

Investigation into the inhibition of anaerobic bacteria was conducted with *Clostridium butyricum* in a disk diffusion assay. Separate α and β hop acids (HYDROHOPS) were employed. This microorganism was found to be very susceptible to the inhibitory properties the alpha hop acid, and not so susceptible with the beta hop acids. Screening data, shown in Table I, below, indicate no synergy between these two compounds at equal concentrations between 0.1 to 1 mg/disk. These data can be corroborated with the aerobic Gram-positive bacteria data, shown in Table II. Further disk diffusion studies indicated a bacteriocidal activity from 5 to 50 mg/disk, and bacteriostatic activity at 1 mg/disk (zones of inhibition are given in Table I below).

Organism: *Clostridium butyricum* (ATCC 3627)

Medium: Oxoid, Reinforced Clostridial Medium, (UNIPATH, Ltd.)

Experimental Procedures

*Clostridum butyricum* microorganism obtained from the American Type Culture Collection (Strain # ATCC 3627), was transferred to fresh RCM agar (Oxoid, Reinforced Clostridial Medium from UNIPATH) 16 hours prior to initiation of the experiment.[1] BBL (blank paper discs (¼" diameter, STN 31039, Becton Dickinson Microbiological Systems)) were sterilized prior to loading with hop acid. Each sterile disk was loaded with hop acid at the desired concentration and allowed to air dry prior to transfer to anaerobic chamber. New RCM agar plates were inoculated with the previously-streaked *C. butyricum* actively growing on RCM plates. This assures that the microorganisms were in a logarithmic growth phase. All disks were aseptically transferred to the plates, and the plates incubated at 35° C. for 48 hours. Clear zones known as "zones of inhibition" were measured with a ruler and their values recorded after 24 and 48 hours incubation. After 48 hours, the plates were removed from the anaerobic chamber and photographed. The data reported for *Clostridium butyricum* represent the diameter of the zones of inhibition; the greater the cleared zone the more active the product or the higher the concentration.

[1] Unipath's instructions were followed for preparing the medium and added DIFCO agar at a concentration of 12.5 g/L. Plates were poured and stored under an anaerobic environment containing carbon dioxide, hydrogen and nitrogen (5, 10 and 85% concentrations, respectively).

The results are shown in Table I, below.

It should be pointed out that these zones of inhibition indicate that, in addition to inhibiting the growth of the microorganism, the microorganisms were killed, since the zone remained clear. These results also indicate that there is at least some degree of aqueous solubility of the active ingredient, because, in order to result in a zone of inhibition, the hop acid must have been soluble to at least some degree (or else the hop acid would not have migrated through the agar).

TABLE I

| Alpha Hop Acid | | | Beta Hop Acid | | | Alpha//Beta Hop Acid | | |
|---|---|---|---|---|---|---|---|---|
| Concentration | Zone of Inhibition (mm) | | Concentration | Zone of Inhibition (mm) | | Concentration | Zone of Inhibition (mm) | |
| (mg/disk) | 24 hr | 48 hr | (mg/disk) | 24 hr | 48 hr | (mg/disk) | 24 hr | 48 hr |
| 1000 | 23 | 23 | 1000 | 15 | 15 | 1000 | 21 | 21 |
| 500 | 23 | 23 | 500 | 15 | 15 | 500 | 20 | 20 |
| 250 | 23 | 23 | 250 | 12 | 12 | 250 | 21 | 32 |
| 100 | 23 | 23 | 100 | 11 | 10 | 100 | 16 | 16 |
| 50 | 20 | 24 | 50 | none | none | | | |
| 25 | 20 | 21 | 25 | none | none | | | |
| 10 | 18 | 19.5 | 10 | none | none | | | |
| 5 | 15 | 14.3 | 5 | none | none | | | |
| 4 | 15 | 13 | 4 | none | none | | | |
| 3 | 13 | 11.5 | 3 | none | none | | | |
| 2 | 12 | 12 | 2 | none | none | | | |
| 1 | 10 | 10 | 1 | none | none | | | |

Example 3

Microtiter Assay

In examining the alpha and beta hops in a microtiter based assay with both Gram-positive and Gram-negative bacteria using a synthetic white water solution, it was found that some of the Gram-negative bacteria were susceptible to the hop acids, but at a much higher concentration (e.g., *Pseudomonas aeruginosa*). This screening evaluation indicated that these compounds, the alpha and beta hop acids, are very effective over a wide concentration range with a variety of different microorganisms. This efficacy demonstrates that these compounds find a use not only in pulp and paper applications, but probably a wide variety of water treatment applications (such as, cooling towers, etc.). The results are set forth in Table II, below.

TABLE II

| Bacterial Strain | pH | Hop Acid | Time (hrs) | $I_{50}$ (ppm) |
|---|---|---|---|---|
| *Klebsiella pneumonia* (ATCC 13883) | 5.5 | Alpha | 4 | 18.07 |
| | | | 24 | >40 |
| | 8.0 | | 4 | >40 |
| | | | 24 | >40 |
| | 5.5 | Beta | 4 | 35.79 |
| | | | 24 | >40 |
| | 8.0 | | 4 | >40 |
| | | | 24 | >40 |
| *Pseudomonas aeruginosa* (ATCC 15442) | 5.5 | Alpha | 4 | 0.357 |
| | | | 24 | >2.5 |
| | 7.2 | | 4 | >2.5 |
| | | | 24 | >2.5 |
| | 8.0 | | 4 | >2.5 |
| | | | 24 | >2.5 |
| | 5.5 | Beta | 4 | 0.036 |
| | | | 24 | >2.5 |
| | 7.2 | | 4 | >2.5 |
| | | | 24 | >2.5 |
| | 8.0 | | 4 | >2.5 |
| | | | 24 | >2.5 |
| *Curtobacterium flaccumfaciens* (BPC 124A) | 5.5 | Alpha | 4 | 0.447 |
| | | | 24 | 0.837 |
| | 7.2 | | 4 | >2.5 |
| | | | 24 | >2.5 |
| | 8.0 | | 4 | 18.72 |
| | | | 24 | >2.5 |
| | 5.5 | Beta | 4 | 0.084 |
| | | | 24 | 0.935 |
| | 7.2 | | 4 | 0.293 |
| | | | 24 | 1.49 |
| | 8.0 | | 4 | 0.748 |
| | | | 24 | 1.72 |
| *Burkholderia cepacia* (BPC 216A) | 5.5 | Alpha | 4 | 25.63 |
| | | | 24 | >40 |
| | 8.0 | | 4 | >40 |
| | | | 24 | >40 |
| | 5.5 | Beta | 4 | 3.67 |
| | | | 24 | 9.26 |
| | 8.0 | | 4 | 6.23 |
| | | | 24 | 6.85 |
| *Pseudomonas glathi* (BPC 322B) | 5.5 | Alpha | 4 | 39.86 |
| | | | 24 | >40 |
| | 8.0 | | 4 | >40 |
| | | | 24 | >40 |
| | 5.5 | Beta | 4 | >40 |
| | | | 24 | >40 |
| | 8.0 | | 4 | >40 |
| | | | 24 | 4.41 |
| *Bacillus cereus* (ATCC 14579) | 5.5 | Alpha | 4 | 0.214 |
| | | | 24 | 0.899 |
| | 8.0 | | 4 | >2.5 |
| | | | 24 | >2.5 |
| | 5.5 | Beta | 4 | 0.033 |
| | | | 24 | 0.230 |
| | 8.0 | | 4 | 0.404 |
| | | | 24 | 0.758 |
| *Bacillus maroccanus* (BPC 223A) | 5.5 | Alpha | 4 | 0.535 |
| | | | 24 | 1.66 |
| | 7.2 | | 4 | >2.5 |
| | | | 24 | >2.5 |
| | 8.0 | | 4 | 17.32 |
| | | | 24 | 33.11 |
| | 5.5 | Beta | 4 | 0.091 |
| | | | 24 | 1.46 |
| | 7.2 | | 4 | 0.579 |
| | | | 24 | >2.50 |
| | 8.0 | | 4 | 0.922 |
| | | | 24 | 1.60 |
| *Bacillus licheniformis* (ATCC 12759) | 5.5 | Alpha | 4 | 0.281 |
| | | | 24 | 0.513 |
| | 8.0 | | 4 | >2.5 |
| | | | 24 | >2.5 |
| | 5.5 | Beta | 4 | 0.026 |
| | | | 24 | 0.324 |
| | 8.0 | | 4 | 0.257 |
| | | | 24 | 0.734 |

TABLE II-continued

| Bacterial Strain | pH | Hop Acid | Time (hrs) | I₅₀ (ppm) |
| --- | --- | --- | --- | --- |
| Bacillus sphaericus (ATCC 4525) | 5.5 | Alpha | 4 | No growth |
| | | | 24 | No growth |
| | 8.0 | | 4 | >2.5 |
| | | | 24 | >2.5 |
| | 5.5 | Beta | 4 | No growth |
| | | | 24 | No growth |
| | 8.0 | | 4 | 0.099 |
| | | | 24 | 0.194 |
| Bacillus subtilis (ATCC 23059) | 5.5 | Alpha | 4 | 0.479 |
| | | | 24 | 0.795 |
| | 8.0 | | 4 | >2.5 |
| | | | 24 | >2.5 |
| | 5.5 | Beta | 4 | 0.026 |
| | | | 24 | 0.09 |
| | 8.0 | | 4 | 0.175 |
| | | | 24 | 0.116 |

Example 4

Effect of Hop Acid on Spores

Experimental: A preparation of spores of *Bacillus cereus* was used for the experiments. Spores were prepared by growing cultures of *B. cereus* in nutrient broth overnight at 37° C. Cultures were harvested by centrifugation and resuspended in sterile distilled water. They were then placed at 80° C. for 15 minutes. After heat treatment, spore preparations were stored at 4° C. for at least 48 hours prior to use. Tests of the effect of L-alanine and hop acid were conducted as follows. Suspensions of *B. cereus* spores were added to sterile water to obtain a spore stock having a concentration of about $10^4$ to $10^5$ spores/ml. The spore stock was then divided into 1.0 ml aliquots for testing. L-alanine was supplied at concentrations of 1 or 2.5 mM. After L-alanine addition, spores were placed at 37° C. for one hour. After L-alanine treatment, hop acid (HYDROHOPS from Watertown Hops, Wisconsion) was added to the spores. After a 20 minute exposure, the spore samples were taken through a serial dilution and plated on nutrient agar medium. Plates were incubated at 37° C. overnight, and after this period, colonies were counted.

The effect of L-alanine was assessed by comparing the plate counts to control spore preparations that were not exposed to L-alanine. To ensure that L-alanine had effectively induced germination spore samples were treated with L-alanine and placed at 80° C. for 15 minutes.

Figure 2:
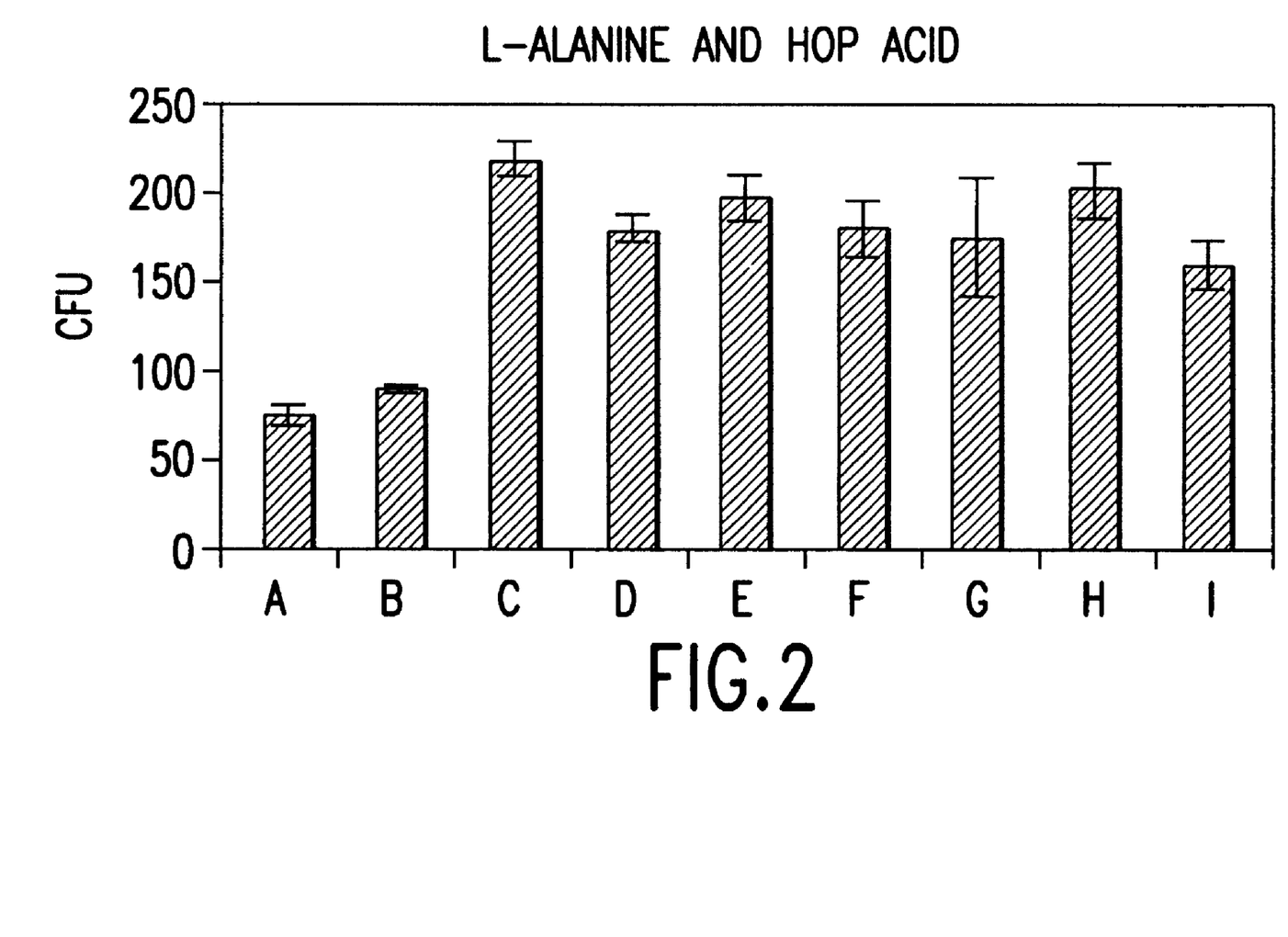
FIG. 2 illustrates results of experiments with hop acids in the treatment of spore-forming bacteria.

Results: As shown in FIG. 2 and TABLE III, control samples A and B show that L-alanine did induce germination, however, killing of germinated cells by hop acid did not occur. This may be due to the fact that hop acid is a more "gentle" or slower acting killing agent than heat or some of the other compounds tested with L-alanine (i.e., dithiol, sulfone/quat blend, glutaraldehyde). The key to FIG. 2 is shown in TABLE III as follows:

TABLE III

| Example No. | L-alanine (mM) | Biocidal Treatment | CFU | SD |
| --- | --- | --- | --- | --- |
| A | 1 | Heat - 80° C., 15 min. | 72 | 6 |
| B | 2.5 | Heat - 80° C., 15 min. | 85 | 1.4 |
| C | 0 | Hop Acid (50 ppm) | 220 | 9.5 |
| D | 0 | Hop Acid (25 ppm) | 180 | 8.2 |
| E | 1.0 | Hop Acid (50 ppm) | 200 | 11.9 |
| F | 2.5 | Hop Acid (50 ppm) | 180 | 16.5 |
| G | 1.0 | Hop Acid (25 ppm) | 176 | 34.5 |

TABLE III-continued

| Example No. | L-alanine (mM) | Biocidal Treatment | CFU | SD |
| --- | --- | --- | --- | --- |
| H | 2.5 | Hop Acid (25 ppm) | 205 | 14.3 |
| I | 0 | Heat - 80° C., 15 min. | 162 | 13.4 |

Example 5

Antifungal Efficacy Study Using Hop Acid

A disk diffusion assay using hop acid treatments was used to evaluate the efficacy of controlling the growth of two fungal species—*Aspergillus niger* and *Chaetomium globosum*. The agar plates used in the experiment were potato dextrose (PDA). Fungal spores were applied as a lawn onto PDA prior to the addition of disks containing hop acid. The disk concentrations used in this experiment were 100, 200, 500, and 1000 ppm.

Plates were incubated at 35° C., and observations made daily. The experiment was terminated after 8 days, and the results from this study indicated that there was growth observed around each disk after sporulation (i.e., no zones of inhibition). This indicated that the hop acid was ineffective in controlling the growth of these two fungi.

CONCLUSION

The foregoing examples indicate that hop acids may not be effective against some spore-forming bacteria, but are effective against vegetative forms of bacteria.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of inhibiting the growth of organisms in an aqueous system selected from a papermaking system, a cooling system or a process water which process water does not contact a final product, wherein the organisms comprise at least one Gram negative bacteria which cause biofouling in said system, comprising adding to the aqueous system an effective amount of one or more hop acids at a pH of at least about 5.5, to inhibit the growth of said organisms in said system.

2. The method of claim 1, wherein the hop acids comprise a member selected from α or β hop acids and mixtures thereof.

3. The method of claim 1, wherein the hop acid comprises one or more members selected from a compound in accordance with one or more of the following formulae:

(I)

wherein "----" represents an optional double bond;
$R_1$ comprises a member selected from OH; and saturated, or unsaturated (containing from about 1 to about 5 double bonds), straight- or branched-chain alkyl or alkenyl of from about 1 to about 20 C atoms;

$R_2$ comprises a member selected from —OH; =O; —SH; =S; and saturated, or unsaturated (containing from about 1 to about 5 double bonds), straight- or branched-chain alkyl or alkenyl of from about 1 to about 20 C atoms;

$R_3$ comprises a member selected from —OH; =O; —SH and =S; and —OOR, wherein R comprises a member selected from H and $C_nH_{2n+1}$, where n is an integer of from about 2 to about 10;

$R_4$ comprises a member selected from saturated or unsaturated (containing from about 1 to about 5 double bonds), straight- or branched-chain alkyl or alkenyl of from about 1 to about 20 C atoms; a ketone of from about 1 to about 20 carbon atoms, a ketone of the general formula C(O)H or $C(O)C_nH_{2n+1}$, where n is an integer of from about 2 to about 10; and —OOR, wherein R comprises a member selected from $C_nH_{2n+1}$ wherein n is an integer of from about 2 to about 10, and H; and/or:

(II)

wherein $R_5$ comprises a ketone of the general formula $C(O)C_nH_{2n+1}$, where n is an integer of from about 2 to about 10;

$R_6$ comprises a member selected from —OH, —SH, and —OOR, wherein R comprises a member selected from $C_nH_{2n+1}$ where n is an integer of from about 2 to about 10; and H;

$R_7$ comprises a member selected from saturated or unsaturated (containing from about 1 to about 5 double bonds), straight- or branched-chain alkyl or alkenyl of from about 1 to about 20 C atoms; and $R_8$ comprises member selected from saturated or unsaturated (containing from about 1 to about 5 double bonds), straight- or branched-chain alkyl or alkenyl of from about 1 to about 20 C atoms; an aldehyde of the general formula C(O)H or a ketone of the general formula $C(O)C_nH_{2n+1}$, where n is an integer of from about 2 to about 10; and/or:

(III)

wherein $R_9$ comprises a saturated, or unsaturated (containing from about 1 to about 5 double bonds), straight- or branched-chain alkyl or alkenyl of from about 1 to about 20 C atoms; and $R_{10}$ comprises a member selected from a ketone of from about 1 to about 20 carbon atoms an aldehyde of the general formula C(O)H, or a ketone of the general formula $C(O)C_nH_{2n+1}$, where n is an integer of from about 2 to about 10; and/or:

(IV)

wherein $R_{11}$ comprises a saturated, or unsaturated (containing from about 1 to about 5 double bonds), straight- or branched-chain alkyl or alkenyl of from about 1 to about 20 C atoms; and $R_{12}$ comprises a member selected from a ketone of from about 1 to about 20 carbon atoms, an aldehyde of the general formula C(O)H, or a ketone of the general formula $C(O)C_nH_{2n+1}$, where n is an integer of from about 2 to about 10.

4. The method of claim 3, wherein $R_4$ comprises a substituent of the formula wherein $R_{13}$ comprises a $C_3$–$C_8$ alkyl group.

5. The method of claim 4, wherein $R_{13}$ comprises a member selected from —$CH_2CH(CH_3)_2$; —$CH(CH_3)_2$; and —$CH(CH_3)_2CH_2CH_3$.

6. The method of claim 5, wherein the hop acid comprises a member selected from hexahydrolupulone; hexahydrocolupulone; hexahydroadlupulone, and mixtures thereof.

7. The method of claim 6, wherein the hop acid comprises hexahydrocolupulone.

8. The method of claim 3, wherein $R_8$ comprises a substituent of the formula wherein $R_{14}$ comprises a $C_3$–$C_8$ alkyl group.

9. The method of claim 8, wherein $R_{14}$ comprises a member selected from $CH_2CH(CH_3)_2$; —$CH(CH_3)_2$; —$(CH_2)_2CH(CH_3)_2$; —$CH(CH_3)_2CH_2CH_3$; and mixtures thereof.

10. The method of claim 9, wherein the hop acid comprises tetrahydroisohumulone.

11. The method of claim 1, wherein the organisms further comprise Gram-positive bacteria.

12. The method of claim 1, wherein the Gram-negative bacteria comprises a member selected from Altermonas, Aquaspirillum, Campylobacter, Helicobacter, Acinetobacter, Agrobacterium, Alcaligenes, Alteromonas, Flavobacterium, Pseudomonas, Xanthomonas, Mycoplasma, Methanococcus mixtures thereof.

13. The method of claim 1, wherein the aqueous system comprises a papermaking system.

14. The method of claim 13 wherein the aqueous papermaking system comprises one or more of refined or unrefined furnish stock in stock tanks; pulp refining conducted in a refiner; refined pulp stored, ready for use in stock chests; paper making furnish drawn from stock chests or flow boxes; or any combination of the foregoing, upstream of the foregoing locations or any point between such locations.

15. The method of claim 13 wherein the hop acids are combined with one or more other papermaking additives.

16. The method of claim 1, wherein the aqueous system comprises a process water.

17. The method of claim 1, wherein the aqueous system comprises a cooling system.

18. The method of claim 13, wherein the hop acids comprise a member selected from α or β hop acids and mixtures thereof.

19. The method of claim 1, wherein the hop acids are present in an amount of from about 0.00 1 to about 1,000 ppm.

20. The method of claim 19, wherein the hop acids are present in an amount of from about 0.1 to about 250 ppm.

21. The method of claim 20, wherein the hop acids are present in an amount of from about 0.1 to about 100 ppm.

22. The method of claim 1, wherein the hop acids are added with a freezing point depressant.

23. A method of inhibiting the growth of organisms in an aqueous system selected from cooling water systems; aqueous systems used in humidifiers; aqueous systems used in heating, ventilating and air conditioning systems; swimming pool water; water used in spas; metal working fluids; petroleum production fluids; paint formulation; plastics processing systems; and mixtures of the foregoing; wherein the organisms comprise at least one Gram negative bacteria which cause biofouling in said system; comprising adding to the aqueous system an effective amount of a hop acid at a pH of at least about 5.5, to inhibit the growth of said organisms in said system.

24. The method of claim 23, wherein the hop acid comprises a member selected from α or β hop acids, and mixtures thereof.

25. The method of claim 23, wherein the hop acid comprises a member selected from a compound in accordance with one or more of the following formulae:

(I)

wherein "----" represents an optional double bond;

$R_1$ comprises a member selected from OH; and saturated, or unsaturated (containing from about 1 to about 5 double bonds), straight- or branched-chain alkyl or alkenyl of from about 1 to about 20 C atoms;

$R_2$ comprises a member selected from —OH; =O; —SH; =S; and saturated, or unsaturated (containing from about 1 to about 5 double bonds), straight- or branched-chain alkyl or alkenyl of from about 1 to about 20 C atoms;

$R_3$ comprises a member selected from —OH; =O; —SH and =S; and —OOR, wherein R comprises a member selected from H and $C_nH_{2n+1}$, where n is an integer of from about 2 to about 10;

$R_4$ comprises a member selected from saturated or unsaturated (containing from about 1 to about 5 double bonds), straight- or branched-chain alkyl or alkenyl of from about 1 to about 20 C atoms; a ketone of from about 1 to about 20 carbon atoms, a ketone of the general formula C(O)H or $C(O)C_nH_{2n+1}$, where n is an integer of from about 2 to about 10; and —OOR, wherein R comprises a member selected from $C_nH_{2n+1}$ wherein n is an integer of from about 2 to about 10, and H; and/or:

(II)

wherein $R_5$ comprises a ketone of the general formula $C(O)C_nH_{2n+1}$, where n is an integer of from about 2 to about 10;

$R_6$ comprises a member selected from —OH, —SH, and —OOR, wherein R comprises a member selected from $C_nH_{2n+1}$ where n is an integer of from about 2 to about 10; and H; and $R_7$ comprises a member selected from saturated or unsaturated (containing from about 1 to about 5 double bonds), straight- or branched-chain alkyl or alkenyl of from about 1 to about 20 C atoms;

$R_8$ comprises member selected from saturated or unsaturated (containing from about 1 to about 5 double bonds), straight- or branched-chain alkyl or alkenyl of from about 1 to about 20 C atoms; an aldehyde of the general formula C(O)H or a ketone of the general formula $C(O)C_nH_{2n+1}$, where n is an integer of from about 2 to about 10; and/or:

(III)

wherein $R_9$ comprises a saturated, or unsaturated (containing from about 1 to about 5 double bonds), straight- or branched-chain alkyl or alkenyl of from about 1 to about 20 C atoms; and $R_{10}$ comprises a member selected from a ketone of from about 1 to about 20 carbon atoms an aldehyde of the general formula C(O)H, or a ketone of the general formula $C(O)C_nH_{2n+1}$, where n is an integer of from about 2 to about 10; and/or:

(IV)

wherein $R_{11}$ comprises a saturated, or unsaturated (containing from about 1 to about 5 double bonds), straight- or branched-chain alkyl or alkenyl of from about 1 to about 20 C atoms; and $R_{12}$ comprises a member selected from a ketone of from about 1 to about 20 carbon atoms, an aldehyde of the general formula C(O)H, or a ketone of the general formula $C(O)C_nH_{2n+1}$, where n is an integer of from about 2 to about 10.

26. The method of claim 25, wherein $R_4$ comprises a substituent of the formula wherein $R_{13}$ comprises a $C_3$–$C_8$ alkyl group.

27. The method of claim 26, wherein $R_{12}$ comprises a member selected from —$CH_2CH(CH_3)_2$; —$CH(CH_3)_2$; and —$CH(CH_3)_2CH_2CH_3$.

28. The method of claim 27, wherein the hop acid comprises a member selected from hexahydrolupulone; hexahydrocolupulone; hexahydroadlupulone, and mixtures thereof.

29. The method of claim 28, wherein the hop acid comprises, hexahydrocolupulone.

30. The method of claim 25, wherein $R_8$ comprises a substituent of the formula wherein $R_{14}$ comprises a $C_3$–$C_8$ alkyl group.

31. The method of claim 30, wherein $R_{14}$ comprises a member selected from $CH_2CH(CH_3)_2$; —$CH(CH_3)_2$; —$(CH_2)_2CH(CH_3)_2$; —$CH(CH_3)_2$ $CH_2CH_3$; and mixtures thereof.

32. The method of claim 31, wherein the hop acid comprises tetrahydroisohumulone.

33. The method of claim 25, wherein the organism further comprises *Pseudomonas aeruginosa*.

34. The method of claim 25, wherein the organism further comprises *Pseudomonas glathi*.

35. The method of claim 25, wherein the hop acid is present in an amount of from about 0.001 to about 1,000 ppm.

36. The method of claim 35, wherein the hop acid is present in an amount of from about 0.1 to about 250 ppm.

37. The method of claim 35, wherein the hop acid is present in an amount of from about 0.1 to about 100 ppm.

* * * * *